United States Patent
Park et al.

(10) Patent No.: US 10,172,571 B2
(45) Date of Patent: Jan. 8, 2019

(54) X-RAY IMAGING APPARATUS

(71) Applicant: OSSTEMIMPLANT CO., LTD., Seoul (KR)

(72) Inventors: Moo-yong Park, Chungju-si (KR); Jae-hee Woo, Suwon-si (KR)

(73) Assignee: OSSTEMIMPLANT CO., LTD., Seoul (KR)

( * ) Notice: Subject to any disclaimer, the term of this patent is extended or adjusted under 35 U.S.C. 154(b) by 143 days.

(21) Appl. No.: 15/308,604

(22) PCT Filed: May 8, 2015

(86) PCT No.: PCT/KR2015/004626
§ 371 (c)(1),
(2) Date: Nov. 2, 2016

(87) PCT Pub. No.: WO2015/170926
PCT Pub. Date: Nov. 12, 2015

(65) Prior Publication Data
US 2017/0188981 A1     Jul. 6, 2017

(30) Foreign Application Priority Data

May 9, 2014   (KR) .................. 10-2014-0055777

(51) Int. Cl.
*A61B 6/03*     (2006.01)
*A61B 6/02*     (2006.01)
(Continued)

(52) U.S. Cl.
CPC ............ *A61B 6/032* (2013.01); *A61B 5/0035* (2013.01); *A61B 6/02* (2013.01); *A61B 6/035* (2013.01);
(Continued)

(58) Field of Classification Search
None
See application file for complete search history.

(56) References Cited

U.S. PATENT DOCUMENTS

| | | | |
|---|---|---|---|
| 9,888,891 B2 * | 2/2018 | Suuronen | A61B 6/4452 |
| 2007/0030950 A1 | 2/2007 | Sa et al. | |
| 2013/0089177 A1 * | 4/2013 | Baldini | A61B 6/14 378/39 |

FOREIGN PATENT DOCUMENTS

| | | |
|---|---|---|
| JP | 11-318886 A | 11/1999 |
| KR | 10-0794563 B1 | 1/2008 |

(Continued)

OTHER PUBLICATIONS

International Search Report for PCT/KR2015/004626 dated Jun. 17, 2015 from Korean Intellectual Property Office.

*Primary Examiner* — Hoon K Song
(74) *Attorney, Agent, or Firm* — Revolution IP, PLLC (57) ABSTRACT

An X-ray imaging apparatus of the present invention includes: a rotation unit disposed on a lower end of a rotation shaft through a sliding part so as to enable a sliding movement along an irradiation direction of X-ray; an X-ray source unit disposed on a lower end of one side of the rotation unit; a sensor unit installed by disposing a shaft rotation part on a lower end of the other side of the rotation unit; a driving unit including: a driving part which provides drive power to the shaft rotation part; and an interlocking part configured to allow the rotation unit to slidably move to one side or the other side according to the rotation state of the shaft rotation part.

7 Claims, 6 Drawing Sheets

(51) Int. Cl.
*A61B 6/14* (2006.01)
*A61B 5/00* (2006.01)
*A61B 6/00* (2006.01)

(52) U.S. Cl.
CPC .............. *A61B 6/14* (2013.01); *A61B 6/4417* (2013.01); *A61B 6/4452* (2013.01); *A61B 6/5247* (2013.01); *A61B 6/588* (2013.01); *A61B 6/589* (2013.01)

(56) References Cited

FOREIGN PATENT DOCUMENTS

| | | |
|---|---|---|
| KR | 10-1034676 B1 | 6/2011 |
| KR | 10-2014-0046725 A | 4/2014 |

* cited by examiner

X-RAY IMAGING APPARATUS

CROSS REFERENCE TO PRIOR APPLICATIONS

This application is a National Stage Application of PCT International Patent Application No. PCT/KR2015/004626 filed on May 8, 2015, under 35 U.S.C. § 371, which claims priority to Korean Patent Application No. 10-2014-0055777 filed on May 9, 2014, which are all hereby incorporated by reference in their entirety.

TECHNICAL FIELD

The present invention relates to an X-ray imaging apparatus, and more particularly, to an X-ray imaging apparatus which can perform both CT imaging and panorama imaging and also implement a rotation of a sensor unit and a sliding movement of a rotation unit with only one driving part, thereby having a simple structure and reducing production costs.

BACKGROUND ART

In general, in dental clinics, X-ray imaging apparatuses are installed to perform X-ray imaging so as to grasp a state of teeth and alveolar bones for the purpose of treating teeth and various types of periodontal disease or performing an orthodontic treatment of teeth set.

In the X-ray imaging apparatuses used in the dental clinics, a predetermined amount of X-rays is transmitted to teeth that are body parts to be imaged, and the intensity of the transmitted X-rays is detected. The transmitted X-rays are converted into an electrical signal corresponding to the intensity of the X-rays and then delivered to a computer. Here, the computer calculates the intensity of the X-rays at each point of the body parts to be imaged and processes the calculation to acquire an image.

An X-ray apparatus for CT (Computer Tomography) capable of imaging a three-dimensional stereoscopic image and an X-ray apparatus for a panorama capable of imaging a two-dimensional planar image are mainly being used as the above-described X-ray apparatuses.

The X-ray imaging apparatus for the CT is an image apparatus that displays a tomogram of the body which is not displayed by the general imaging. That is, the X-ray imaging apparatus for the CT is a topographic apparatus that emits X-rays to the human body while rotating at a constant angle over 360 degree and then collects the transmitted X-rays by a detector such as a sensor to reconstruct an absorbing rate on the tomogram of the human body, thereby displaying an image.

Alternatively, the X-ray image apparatus for panorama images as the entirety in a circumferential direction around an X-ray generator. That is, the X-ray image apparatus for the panorama is an apparatus capable of performing the panorama imaging so that states of the whole teeth and temporomandibular joints are viewed at a glance.

However, the X-ray imaging apparatus for the CT may acquire only the tomographic image. On the other hand, the X-ray imaging apparatus for the panorama may acquire only the panoramic image.

That is, the X-ray imaging apparatus for the CT may acquire only the CT image, and the X-ray imaging apparatus for the panorama may acquire only the panoramic image.

Therefore, in recent years, apparatuses in which both the CT imaging and the panorama imaging are performed by using one X-ray imaging apparatus are being proposed.

PRIOR ART DOCUMENTS

Patent Registration No. 10-0794563 (Registration date: Jan. 8, 2008)

DISCLOSURE OF THE INVENTION

Technical Problem

The purpose of the present invention to solve the above-described problems according to the related art is to provide an X-ray imaging apparatus which is capable of performing both CT imaging and panorama imaging and also realizing rotation of a sensor unit and sliding movement of a rotation unit by using only one driving part to embody a simple structure and reduce production costs.

Technical Solution

To solve the technical problems described above, an X-ray imaging apparatus according to the present invention includes a rotation unit disposed on a lower end of a rotation shaft through a sliding part so as to enable a sliding movement along an irradiation direction of X-ray; an X-ray source unit disposed on a lower end of one side of the rotation unit; a sensor unit installed by disposing a shaft rotation part on a lower end of the other side of the rotation unit and including a first sensor at one side thereof and a second sensor at the other side thereof; and a driving unit including: a driving part which provides drive power to the shaft rotation part so as to be converted to a first rotation state in which the first sensor faces the X-ray source unit or a second rotation state in which the second sensor faces the X-ray source unit; and an interlocking part configured to allow the rotation unit to slidably move to one side or the other side according to the rotation state of the shaft rotation part.

Preferably, the interlocking part may include: a first hinge disposed at a point on a rotation radius of the shaft rotation part; a second hinge disposed at a point in the sliding part; and an interlocking link of which one end is rotatably connected to the first hinge and the other end is rotatably connected to the second hinge.

Preferably, the shaft rotation part may include: a hollow fixed body that passes through the lower end of the other side of the rotation unit and is fixedly coupled to the lower end of the other side of the rotation unit; and a hollow rotation body that is installed to be relatively rotatable in a coaxial manner with respect to the hollow fixed body and has a lower end on which a sensor body is installed, wherein a first sensor is disposed in one side of the sensor body, and a second sensor is disposed in the other side of the sensor body, and the first hinge protrudes in a pin shape from an upper portion of the hollow rotation body.

Preferably, the driving part may include: a first gear disposed in an outer circumferential surface of the hollow rotation body; a second gear engaged with the first gear; and a driving motor configured to rotate the second gear.

Preferably, the sliding part may include: a fixed plate fixedly coupled to a lower end of the rotation shaft in a vertical direction; a guide block disposed on a top surface of the fixed plate; and a guide rail disposed on a corresponding surface of the rotation unit, which corresponds to the top surface of the fixed plate so as to be rail-coupled to the guide block, wherein the second hinge protrudes in a pin shape from a point of the fixed plate.

Preferably, an elastic part that may elastically pull the fixed plate to the source unit is provided.

Preferably, a longitudinal hole through which the rotation shaft passes may be defined in the rotation unit, a pair of guide rails may be fixedly installed on a bottom surface of the rotation unit, which corresponds to both sides of the longitudinal hole, and the guide block may be fixedly installed on each of the top surfaces of both sides of the fixed plate to correspond to each of the pair of guide rails.

Preferably, a length adjusting part may be disposed at a central portion of the interlocking link.

Advantageous Effects

The present invention as described above may perform both the CT imaging and the panorama imaging and also realize the rotation of the sensor unit and the sliding movement of the rotation unit by using the only one driving part to embody the simple structure and reduce production costs.

Also, as the result of realizing the rotation of the sensor unit and the sliding movement of the rotation unit by using the only one driving part, the distance between the X-ray source unit and the sensor unit may be uniformly maintained. On the other hand, the distance between the X-ray source unit and the examinee may be changed so that the two imaging processes are enabled by adequately adjusting the magnification for the panorama image photographing or the CT imaging.

Also, the rotation of the sensor unit and the sliding movement of the rotation unit are interlocked with each other to achieve the simple structure through the simple link structure in which the pair of protruding pins are connected to the interlocking link.

Also, the length adjusting part may be disposed at the central portion of the interlocking link to finely adjust the interlock of the rotation of the sensor unit and the sliding movement of the rotation unit.

Also, the fixed plate may be prevented from being spaced from the rotation unit through the elastic part that elastically pulls the fixed plate to the source unit.

MODE FOR CARRYING OUT THE INVENTION

The present invention may be realized in other various forms without departing from the technical idea or the essential feature. Thus, the embodiments of the present invention may be merely illustrative in all aspects and should not be construed as limited thereto.

Although the terms such as first and second are used herein to describe various elements, these elements should not be limited by these terms.

The terms are only used to distinguish one element from other elements. For example, a first element can be referred to as a second element, and similarly a second element can be referred to as a first element without departing from the scope of the present invention.

The term 'and/or' includes a combination of a plurality of items relevantly described or any one of a plurality of items relevantly described.

It will also be understood that when an element is referred to as being "'connected to" or "engaged with" another element, it can be directly connected to or engaged with the other element, or intervening elements may also be present.

On the other hand, it will be understood that when an element is referred to as being "directly connected to" or "directly engaged with" another element, there is no intervening elements.

In the present application, the terms are used only for explaining a specific exemplary embodiment and are not intended to limit the present invention. The terms of a singular form may include plural forms unless definitely indicating a particular case in terms of the context.

In the present application, it will be understood that the terms of 'include', 'comprise', or 'have' specifies the presence of a feature, a fixed number, a step, a process, an element, a component, or a combination thereof disclosed in the specification, but does not exclude a possibility of the presence or addition of one or more other features, fixed numbers, steps, processes, elements, components, or combinations thereof.

Unless otherwise defined, all terms (including technical and scientific terms) used herein have the same meaning as generally understood by those skilled in the art to which the present invention pertains.

Terms as defined in a commonly used dictionary should be construed as having the same meaning as in an associated technical context, and unless defined apparently in the present application, the terms are not ideally or excessively construed as having formal meaning.

Hereinafter, preferred embodiment according to the present invention is described in detail with reference to the accompanying drawings, and the same or corresponding elements are given with the same reference numeral regardless of the figure number, and their duplicated description will be omitted.

In the description of the present invention, if a detailed description related to well-known technology is determined to obscure subject matters of the present invention, the detailed description may be omitted.

Figure 1:
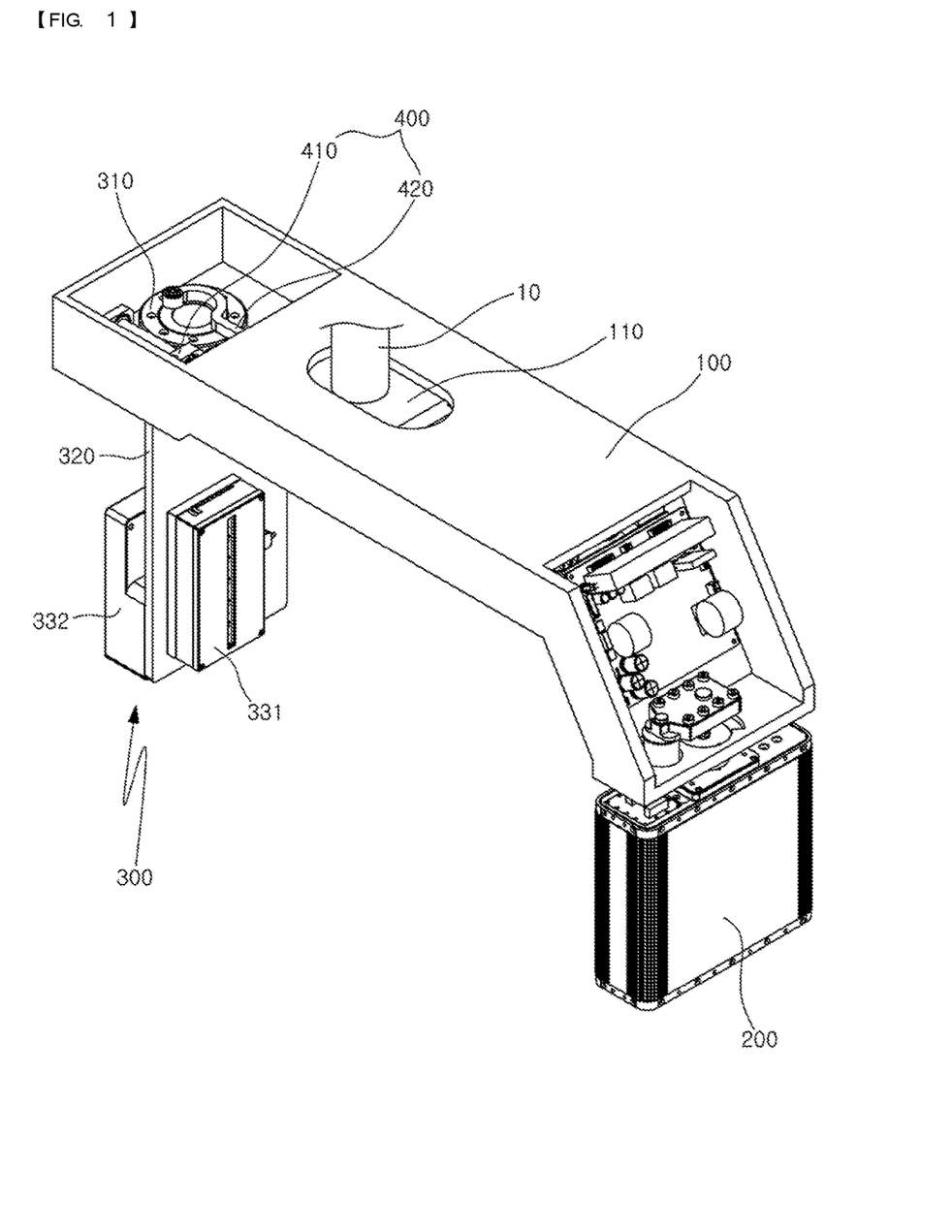
FIG. 1 is a perspective view of an X-ray imaging apparatus according to an embodiment of the present invention.
Figure 2:
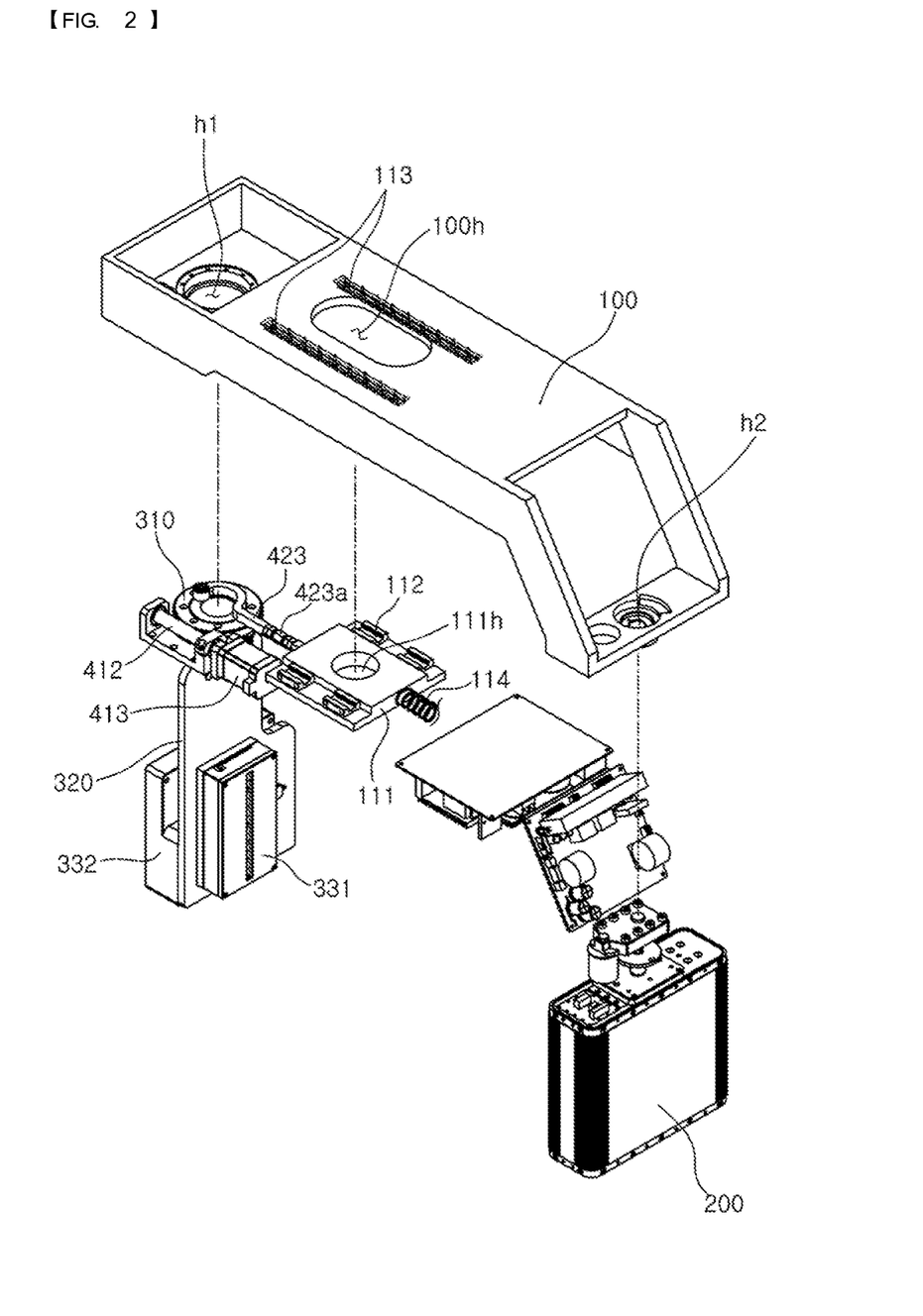
FIG. 2 is an exploded perspective view of an X-ray imaging apparatus according to an embodiment of the present invention.

An X-ray imaging apparatus according to an embodiment of the present invention includes a rotation unit 100, an X-ray unit 200, a sensor unit 300, and a driving unit 400 as illustrated in FIGS. 1 and 2.

As illustrated in FIG. 1, the rotation unit 100 is disposed on a lower end of a rotation shaft 10 through a sliding part 110 and is capable of slidably moving along an irradiation direction of X-ray.

Particularly, the rotation unit 100 is a frame extending along the irradiation direction of the X-ray and has a longitudinal hole 100$h$ defined in a central portion of the rotation unit 100. Also, the rotation shaft 10 is disposed to pass through the longitudinal hole 100$h$.

Therefore, the rotation unit 100 may slidably move in a longitudinal direction of the longitudinal hole 100h along the irradiation direction of X-ray without any interference with the rotation shaft 10.

Figure 3:
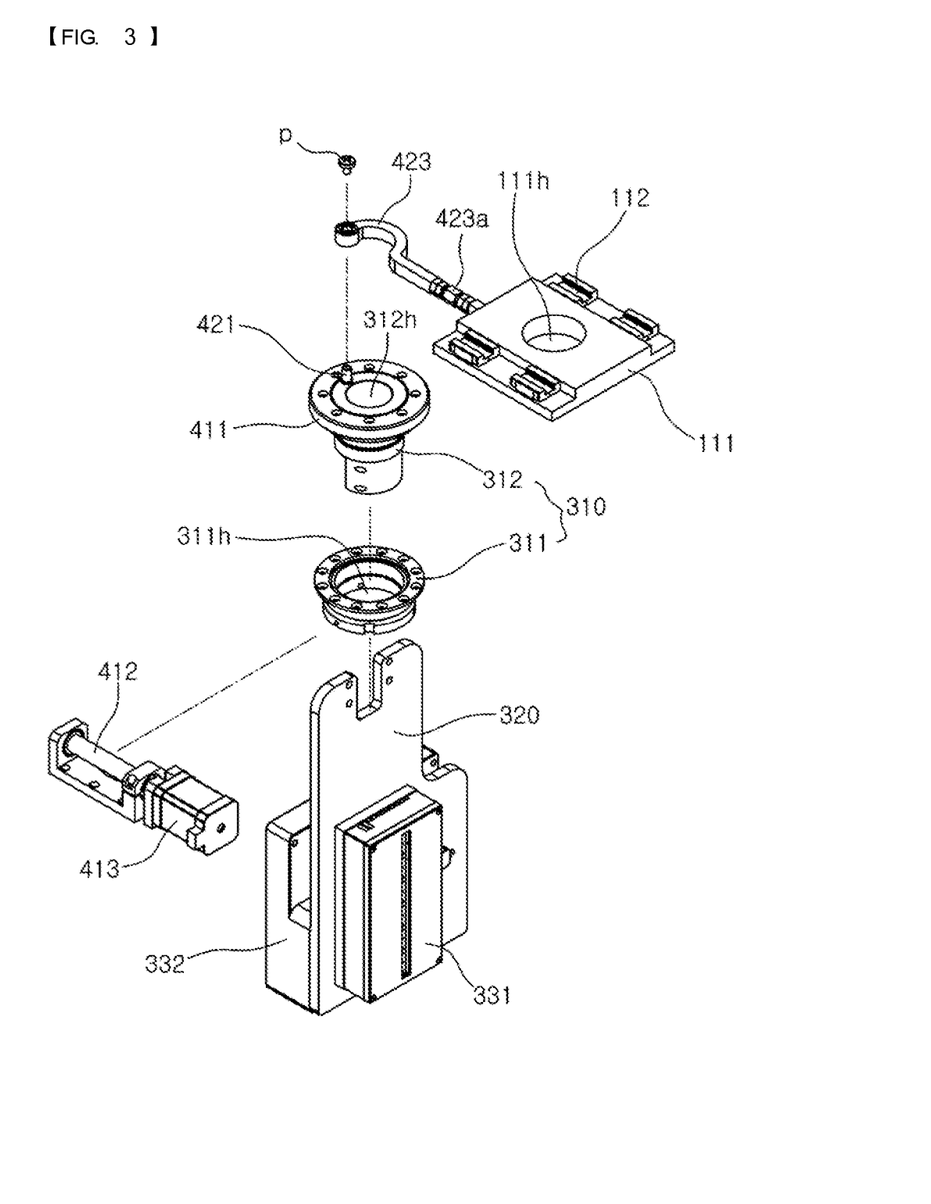
FIG. 3 is an exploded perspective view illustrating a portion of components of an X-ray imaging apparatus according to an embodiment of the present invention.

As illustrated in FIGS. 2 and 3, the sliding part 110 includes a fixed plate 111 fixedly coupled to the lower end of the rotation shaft 10 in a vertical direction, a guide block 112 disposed on a top surface of the fixed plate 111, a guide rail 113 disposed on a corresponding surface of the rotation unit 100, which corresponds to the top surface of the fixed plate 111 so that the guide rail 113 is rail-coupled to the guide block 112.

The fixed plate 111 is a plate member. A rotation shaft coupling hole 111h is defined in a central portion of the fixed plate 111 to insert and fixedly couple the end of the rotation shaft 10 thereto. Also, a stepped portion is disposed on each of top surfaces of both sides of the fixed plate 111 to fixedly install the guide block 112 on each of surfaces of the stepped portions.

The guide block 112 may be disposed in plurality in a sliding direction of the rotation unit 100. For example, the guide block 112 may be installed in a 2×2 matrix array as illustrated in FIG. 2, and preferably constituted by a LM guide.

The guide rail 113 is disposed on the corresponding surface of the rotation unit 100 facing the guide block 112. Particularly, the guide rail 113 may be fixedly installed on an inner bottom surface of the rotation unit 100.

For example, the guide rail 113 may be constituted by a pair of LM rails on the bottom surface of the rotation unit 100 corresponding to both sides of the longitudinal hole 100h.

As described above, the rotation unit 100 may be slidably movable relatively with respect to the rotation shaft 10 along the irradiation direction of X-rays through the sliding part 110 including the fixed plate 111, the guide block 112, and the guide rail 113.

Also, the fixed plate 111 is configured to be elastically pulled to the X-ray source unit 200. For this, an elastic part 114 is disposed to elastically pull the fixed plate 111 to the X-ray source unit 200.

For example, as illustrated in FIG. 2, the elastic part 114 may be constituted by an elastic body such as a spring of which one end is connected to a surface of the fixed plate 111 and the other end is connected a point of the rotation unit 100.

The elastic part 114 elastically pulls the fixed plate to the X-ray source unit 200 all the time, and thus functions of preventing the fixed plate 111 from minutely vibrating.

Also, a second hinge (see reference numeral 422 in FIG. 6) protrudes in a pin shape from a point of the fixed plate 111, for example, a bottom surface of the fixed plate 111. The second hinge will be described in more detail when an interlocking part 420 is described.

According to the constitutions of the rotation unit 100 as described above, the rotation unit 100 is slidably movable along the irradiation direction of the X-ray through the sliding part 110, and vibrating of the fixed plate 111 is prevented by the elastic part 114.

The X-ray source unit 200 is disposed in a lower end of one side of the rotation unit 100. Particularly, the X-ray source unit 200 is shaft-coupled to an X-ray source unit coupling hole h2 defined in the lower end of one side of the rotation unit 100 as illustrated in FIG. 2.

The X-ray source unit 200 is a part that generates X-ray to irradiate the X-ray to the sensor unit 300. The X-ray irradiated from the X-ray source unit 200 may pass through a head portion of an examinee and then be detected by a first sensor 331 or a second sensor 332 of the sensor unit 300.

That is, the X-ray for the X-ray imaging may be irradiated to the sensor unit 300 through the above-described X-ray source unit 200.

As illustrated in FIGS. 1 to 3, the sensor unit 300 includes a sensor body 320 installed by disposing a shaft rotation part 310 in a lower end of the other side of the rotation unit 100, the first sensor 331 disposed in one side of the sensor body 320, and the second sensor 332 disposed in the other side of the sensor body 320.

As illustrated in FIG. 3, the sensor body 320 is a member having an approximately plate shape and includes the first sensor 331 on one side surface of the sensor body 320 and the second sensor 332 on the other side surface of the sensor body 320.

For example, the first sensor 331 may be constituted by a sensor for the panorama imaging, and the second sensor 332 may be constituted by a sensor for the CT imaging.

Also, the sensor body 320 is installed by disposing the shaft rotation part 310 in the lower end of the other side of the rotation unit 100. Particularly, as illustrated in FIG. 3, the shaft rotation part 310 includes a hollow fixed body 311 that passes through the lower end of the other side of the rotation unit 100 and is fixedly coupled to the lower end of the other side of the rotation unit and a hollow rotation body 312 that is installed to be relatively rotatable in a coaxial manner with respect to the hollow fixed body 311 and has a lower end on which the sensor body 320 is disposed.

Particularly, the hollow fixed body 311 is fixedly coupled to a sensor unit coupling hole h1 defined in the lower end of the other side of the rotation unit 100, and the hollow rotation body 312 is inserted into the hollow fixed body 311 so that the hollow rotation body 312 is installed to be relatively rotatable in the coaxial manner with respect to the hollow fixed body 311.

The hollow fixed body 311 and the hollow rotation body 312 may be, for example, assembled with each other in the coaxial manner through a rolling unit such as a bearing. Therefore, the hollow rotation body 312 may be constituted to be rotatable with respect to the hollow fixed body 311.

Also, a first hinge 421 protrudes in a pin shape at a point on a rotation radius in an upper portion of the rotation body 312. The first hinge 421 will be described in more detail when the interlocking part 420 is explained.

According to the constitutions of the sensor unit 300 as described above, the sensor body 320 is rotatable through the shaft rotation part 310. Therefore, the first sensor 331 or the second sensor 332 may selectively detect the X-ray of the X-ray source unit 200.

The driving unit 400 includes a driving part 410 and the interlocking part 420.

The driving part 410 is a part that provides driving force to the shaft rotation part 310. As rotational driving force is provided to the shaft rotation part 310, a first rotation state in which the first sensor 331 faces the X-ray source unit 200 may be converted to a second rotation state in which the second sensor 332 faces the X-ray source unit 200.

The driving part 410 includes a first gear 411 disposed in an outer circumferential surface of the hollow rotation body 312, a second gear 412 engaged with the first gear 411, a diving motor 413 configured to rotate the second gear 412.

Thus, when the second gear 412 rotates by driving of the driving motor 413, the first gear 411 engaged with the second gear 412 rotates, and then the hollow rotation body 312 rotates by a rotation of the first gear 411.

The first gear 411 is constituted by a worm gear, and the second gear 412 is constituted by a worm-wheel gear.

Also, the driving motor 413 may be constituted by a servo motor capable of controlling the number of turns. Thus, the driving motor 413 may provide the rotational driving force so as to be accurately converted to the first rotation state in which the first sensor 331 faces the X-ray source unit 200 or the second rotation state in which the second sensor 332 faces the X-ray source unit 200 as rotating at an angle of 180° from the first rotation state.

Figure 5:
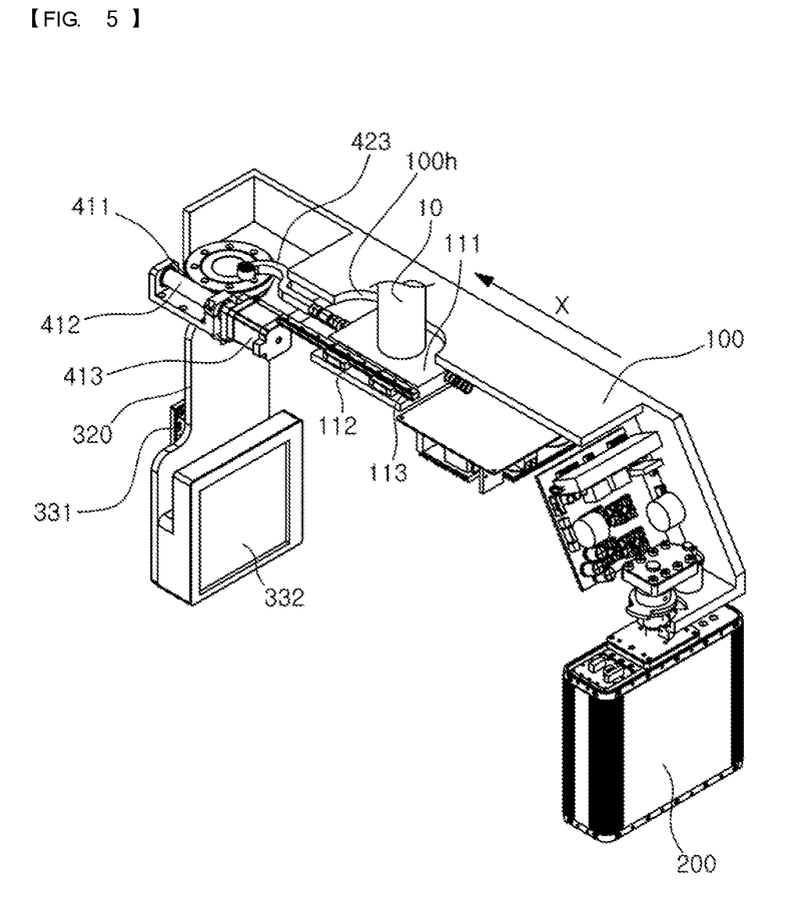

The interlocking part 420 is a part that slidably moves the rotation unit 100 to one side or the other side in a direction X of FIG. 5 in response to a rotational state of the shaft rotation part 310. The interlocking part 420 includes the first hinge 421 disposed at a point on the rotation radius of the shaft rotation part 310, the second hinge 422 disposed at a point in the sliding part 110, and an interlocking link 423 of which one end is rotatably connected to the first hinge 421 and the other end is rotatably connected to the second hinge 422.

That is, the interlocking part 420 is a part that slidably moves the rotation unit 100 to one side or the other side by the link driving due to the interlocking of the first hinge 421, the second hinge 422, and the interlocking link 423 when the hollow rotation body 312 constituting the shaft rotation part 310 rotates by the driving part 410.

Also, a length adjusting part 423a is disposed in a central portion of the interlocking link 423, and an initial position of the sensor body 320 is accurately adjusted by the length adjusting part 423a to accurately adjust initial positions of the first sensor 331 and the second sensor 332.

That is, the first rotation state in which the first sensor 331 faces the X-ray source unit 200 or the second rotation state in which the second sensor 332 faces the X-ray source unit 200 may be accurately adjusted.

Also, it is preferable that an end of the interlocking link 423 connected to the first hinge 421 is formed in a semi-circular shape to prevent the interlocking link 423 from being interfered with a power line and a data line, and the like connected to the first sensor 331 and the second sensor 332 through the inside of the hollow rotation body 321.

According to the constitutions of the driving unit 400 as described above, any one of the first sensor 331 and the second sensor 332 may rotate to face the X-ray source unit 200 by the driving part 410, and the rotation unit 100 is interlocked with the rotation to slide to one side or the other side.

Hereinafter, as described above, an operation of the X-ray imaging apparatus will be described.

Figure 4:
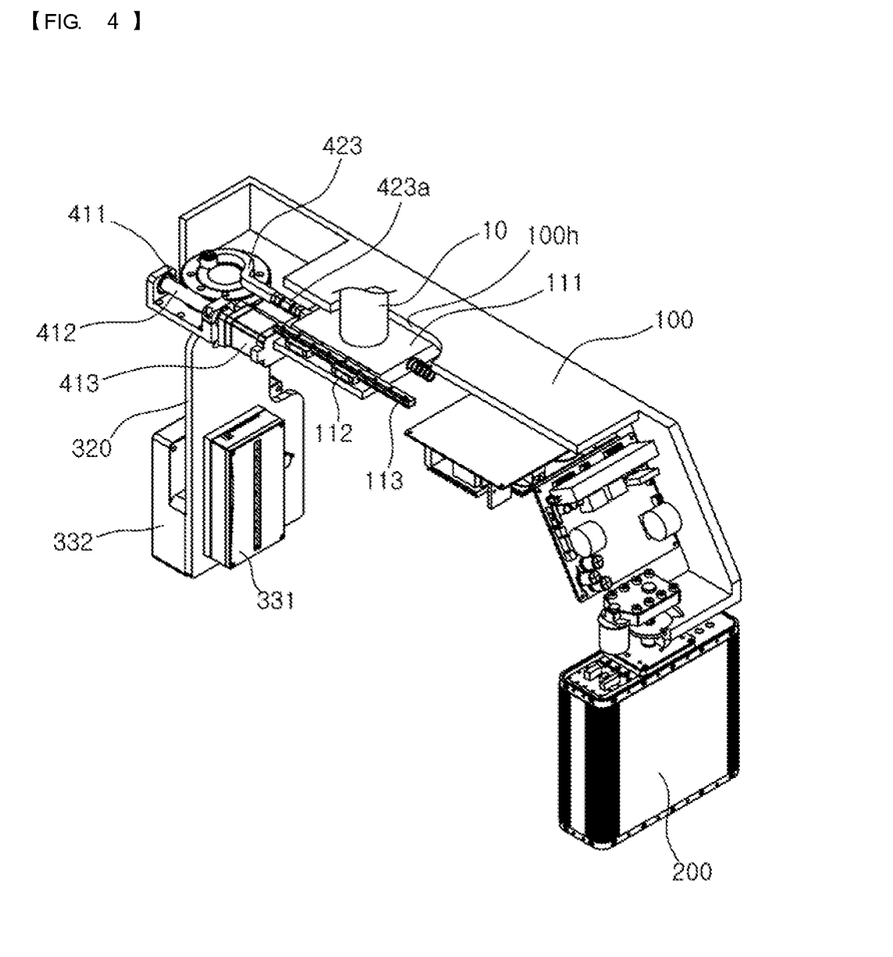
FIGS. 4 and 5 are perspective views illustrating operating states of an X-ray imaging apparatus according to an embodiment of the present invention.
Figure 6:
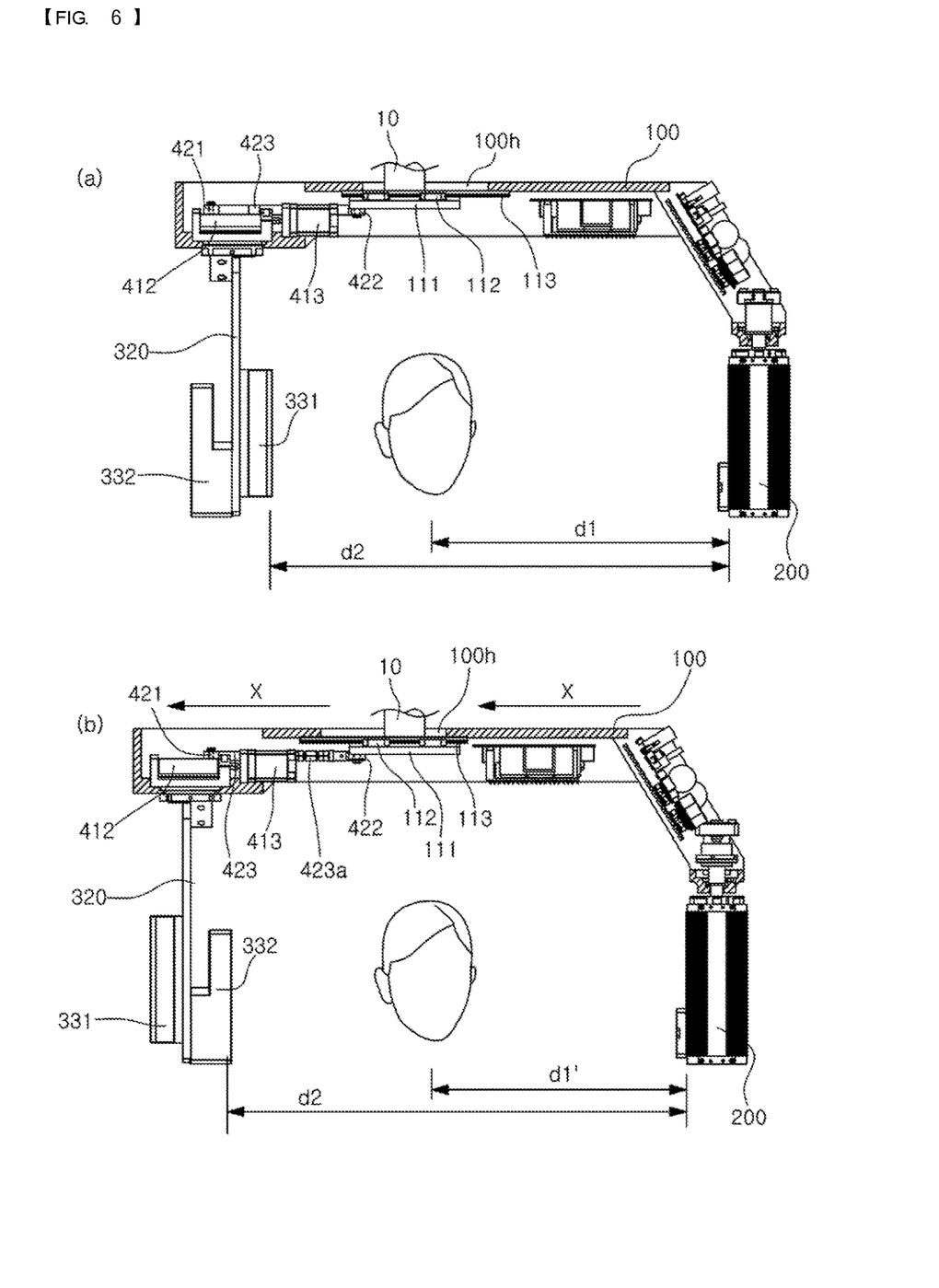
FIG. 6 is front views illustrating operating states of an X-ray imaging apparatus according to an embodiment of the present invention.

As illustrated in FIG. 4 or 6(a), in the first rotation state in which the sensor for the panorama imaging which is the first sensor 331 rotates to face the X-ray source unit 200, the panorama image photographing may be available.

Here, when a distance between the X-ray source unit 200 and the examinee is 'd1', and a distance between the X-ray source unit 200 and the first sensor 331 is 'd2', the panorama image photographing at a set magnification may be performed.

In this state, as illustrated in FIG. 5 or (b) of FIG. 6, the driving motor 413 may rotate the second gear 412 to rotate the first gear 411, and the hollow rotation body 312 may rotate by the rotation of the first gear 411. Thus, the hollow rotation body 312 may rotate at an angle of 180° to convert the above-described state to the second rotation state in which the sensor for the CT imaging which is the second sensor 332 rotates to face the X-ray source unit 200. Therefore, the CT image photographing may be available.

Also, the first hinge 421 disposed on the hollow rotation body 312 is moved to a position adjacent to the source unit by the rotation of the hollow rotation body 312 at an angle of 180°. Therefore, the rotation unit 100 slidably moves in an 'X' direction of the drawings with respect to the fixed plate 111 by a link operation of the interlocking link 423 and the second hinge 422.

Thus, although the distance between the X-ray source unit 200 is maintained as 'd2', the distance between the X-ray source unit 200 and the examinee is 'd2''. Therefore, the imaging magnification for the CT imaging may be adjusted to perform the CT imaging.

Although the present invention has been described with reference to the accompanying drawings with respect to preferred embodiments, it should be understood that various and obvious modifications can be made from this disclosure without departing from the scope of the present invention by those skilled in the art. Hence, the scope of the present invention has to be analyzed by the appended claims to include such modifications.

The invention claimed is:

1. An X-ray imaging apparatus comprising:
   a rotation unit disposed on a lower end of a rotation shaft through a sliding part so as to enable sliding movement along an irradiation direction of X-rays;
   an X-ray source unit disposed on a lower end of one side of the rotation unit;
   a sensor unit installed by disposing a shaft rotation part on a lower end of the other side of the rotation unit and comprising a first sensor at one side thereof and a second sensor at the other side thereof; and
   a driving unit comprising a driving part which provides drive power to the shaft rotation part so as to be converted to a first rotation state in which the first sensor faces the X-ray source unit or a second rotation state in which the second sensor faces the X-ray source unit and an interlocking part configured to allow the rotation unit to slidably move to one side or the other side according to the rotation state of the shaft rotation part,
   where the interlocking part comprises:
   a first hinge disposed at a point on a rotation radius of the shaft rotation part;
   a second hinge disposed at a point in the sliding part; and
   an interlocking link of which one end is rotatably connected to the first hinge and the other end is rotatably connected to the second hinge.

2. The X-ray imaging apparatus of claim 1, wherein the shaft rotation part comprises:
   a hollow fixed body that passes through the lower end of the other side of the rotation unit and is fixedly coupled to the lower end of the other side of the rotation unit; and
   a hollow rotation body that is installed to be relatively rotatable in a coaxial manner with respect to the hollow fixed body and has a lower end on which a sensor body is installed,
   wherein a first sensor is disposed in one side of the sensor body, and a second sensor is disposed in the other side of the sensor body, and
   the first hinge protrudes in a pin shape from an upper portion of the hollow rotation body.

3. The X-ray imaging apparatus of claim 2, wherein the driving part comprises:
   a first gear disposed in an outer circumferential surface of the hollow rotation body;
   a second gear engaged with the first gear; and
   a driving motor configured to rotate the second gear.

4. The X-ray imaging apparatus of claim 1, wherein the sliding part comprises:
- a fixed plate fixedly coupled to a lower end of the rotation shaft in a vertical direction;
- a guide block disposed on a top surface of the fixed plate; and
- a guide rail disposed on a corresponding surface of the rotation unit, which corresponds to the top surface of the fixed plate, so as to be rail-coupled to the guide block,
- wherein the second hinge protrudes in a pin shape from a point of the fixed plate.

5. The X-ray imaging apparatus of claim 4, wherein an elastic part that elastically pulls the fixed plate to the source unit is provided.

6. The X-ray imaging apparatus of claim 4, wherein a longitudinal hole through which the rotation shaft passes is defined in the rotation unit,
- a pair of guide rails are fixedly installed on a bottom surface of the rotation unit, which corresponds to both sides of the longitudinal hole, and
- the guide block is fixedly installed on each of the top surfaces of both sides of the fixed plate to correspond to each of the pair of guide rails.

7. The X-ray imaging apparatus of claim 1, wherein a length adjusting part is disposed at a central portion of the interlocking link.

* * * * *